United States Patent
Berestov

(10) Patent No.: US 6,222,904 B1
(45) Date of Patent: Apr. 24, 2001

(54) STEREO X-RAY ANTI-SCATTER GRID

(75) Inventor: Alexander Berestov, San Jose, CA (US)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/359,960

(22) Filed: Jul. 22, 1999

(51) Int. Cl.$^7$ ........................................................ A61B 6/02
(52) U.S. Cl. .......................... 378/41; 378/210; 378/154; 378/901
(58) Field of Search .............................. 378/41, 210, 154, 378/147

(56) References Cited

U.S. PATENT DOCUMENTS

| | | |
|---|---|---|
| 1,447,399 | * 3/1923 | Pease . |
| 4,287,420 | * 9/1981 | Yamamura et al. . |
| 5,365,562 | * 11/1994 | Toker . |
| 5,818,064 | * 10/1998 | Kohgami et al. . |
| 6,061,424 | * 5/2000 | Hoppenstein et al. . |

OTHER PUBLICATIONS

Canon U.S.A., Inc., advertisement for Canon Digital Radiography System, 1997, Lake Success, NY.

Bushong, Stewart C., "Radiologic Science for Technologist" Chapter 18, pp 214–228, 1997, St. Louis, MO.

Yamazaki, Tatsuya, et al., "Development of Digital Radiography System," Computer Assisted Radiology and Surgery, Proceedings of the 12$^{th}$ International Symposium and Exhibition, Tokyo, Japan, Jun. 24–27, 1998, pp. 536–541.

Kameshima, Toshio, et al., "Novel Large Area MIS–type X–ray Image Sensor for Digital Radiography," Part of the SPIE Conference on Physics of Medical Imaging, pp. 453–462, Feb. 1998, San Diego, CA.

"Digital Imaging and Communications in Medicine (DICOM) Supplement 32: Digital X–Ray Supplement," Sep. 1, 1998, American Dental Association, Chicago, IL.

* cited by examiner

*Primary Examiner*—Robert H. Kim
*Assistant Examiner*—Pamela R. Hobden
(74) *Attorney, Agent, or Firm*—Fenwick & West LLP

(57) ABSTRACT

A stereo radiograph is produced in a radiography system including an anti-scatter grid (105) and sensor material (107). At least one x-ray beam (102) is emitted towards a body to be radiographed (103). The anti-scatter grid (105) is focused so as to transmit two distinct x-ray beams (106) to the sensor material (107). The transmitted beams (106) create two alternating images on the sensor material (107). A stereo radiograph is created from the two alternating images. System geometry of the radiography system is used to determine location of an object (606) within a radiographed body (103), and to determine distance (613) between a chosen point and an object (606) within a radiographed body (103).

28 Claims, 6 Drawing Sheets

STEREO X-RAY ANTI-SCATTER GRID

TECHNICAL FIELD

This invention pertains to the use of an x-ray anti-scatter grid to produce a stereo image in a radiography system.

BACKGROUND ART

Anti-Scatter Grids

An anti-scatter grid is a physical device that blocks scattered radiation. When a primary x-ray beam interacts with a body, secondary x-rays are scattered in all directions. Secondary x-rays that are traveling in a direction other than that of the primary beam cause a radiographic fog in the x-ray image. Such radiographic fog reduces the contrast of the image.

An anti-scatter grid comprises alternating sections of radiopaque material (typically lead) and radiolucent material (typically aluminum), encased in a protective, radiolucent housing. An anti-scatter grid is designed to absorb only the x-rays traveling in a direction other than that of the primary beam.

Various technical parameters of an anti-scatter grid determine its effectiveness under different conditions. An anti-scatter grid may be parallel or focused. In a parallel grid, all of the radiopaque sections are parallel to each other, and perpendicular to the surface of the grid. In a focused grid, the radiopaque sections are progressively tilted such that straight lines extended from the points at which the sections intersect with the surface of the grid would intersect at a single point. This point is defined as the focal point of the grid. Parallel grids are less expensive to manufacture than focused grids, but have the undesirable effect of absorbing more of the primary x-rays. Focused grids absorb less primary radiation, but unlike parallel grids must be used at an appropriate focal distance from the beam source, plus or minus an acceptable margin of error.

Both parallel and focused grids may be linear or crossed. A linear grid comprises a single parallel or focused anti-scatter grid. A crossed grid comprises two linear grids, one on top of the other, such that the radiopaque sections of one grid are perpendicular to those of the other. Crossed grids absorb a significantly higher percentage of the scattered radiation than linear grids, but must be positioned much more carefully relative to the source of the x-ray beam. All grids may also be fixed in position, or moving. Moving grids are attached to a mechanism that is moved as the x-rays pass through the body radiographed. This has the effect of minimizing, in the x-ray image, lines caused by the absorbence of primary x-rays by the grid.

Other technical parameters of the grid are the specific radiopaque and radiolucent materials used, the width of the sections of radiopaque material, the width of the sections of radiolucent material, the height of the grid, the ratio of the height of the grid to the width of the sections of radiopaque material (called the grid aspect ratio), the focal distance of the grid (relevant for focused grids only), and the period of time for which the grid is in motion while the digital sensor plate is being exposed to radiation (relevant for moving grids only). All of these factors determine the extent to which a grid absorbs secondary radiation, the extent to which a grid undesirably absorbs primary radiation, the proper range of focal distances for the grid, the tolerance of the grid for use outside of that range, and the dose of radiation to which the body being radiographed must be exposed in order to generate a useful x-ray image.

Anti-scatter grids are commonly used in radiography systems. Existing anti-scatter grids transmit radiation traveling in the direction of a single primary beam, so as to produce a single radiographic image.

Three Dimensional Radiographic Images

The inherent limitation of two dimensional images is a serious shortcoming of radiography as it exists today. It is desirable for a physician or researcher to know exactly where an object is located within a radiographed body. Although a two dimensional radiographic image presents an internal view of a body, it is difficult to recognize three dimensional structure within a body from a two dimensional radiograph.

There exist several rather complicated techniques for determining three dimensional information within a body. Three dimensional information can be obtained by transmission x-ray microscopy, a combination of an x-ray transmission technique with tomographical reconstruction. This combination allows the obtaining of three dimensional information about the internal microstructure of an object. An internal area is reconstructed as a set of flat cross sections which are used to analyze two and three dimensional morphological parameters. The contrast in the resulting radiographic images is a mixed combination of density and compositional information.

In some cases the compositional information can be separated form the density information with the help of a Computed Axial Tomography scan (CAT scan). A CAT scan is a medical diagnostic procedure that combines the use of x-rays with computer technology. A series of x-ray beams from many different angles are used to create cross-sectional images of a patient's body. These images are assembled by a computer into a three dimensional picture that can display organs, bones, and tissues in great detail.

However, these facilities are very complicated and expensive, and thus are not accessible for most researchers and users. What is needed is an inexpensive and readily accessible method for creating a stereo radiographic image, from which an exact location of an object within a body can be determined. This information has many important medical applications, such as surgery, physical therapy, and the like.

DISCLOSURE OF INVENTION

The present invention is a method, computer program product, and radiography system for using an anti-scatter grid (105) to produce a stereo radiographic image. A beam of x-rays (102) is emitted from an x-ray source (101) towards a body (103) to be radiographed. An anti-scatter grid (105) is focused such that the anti-scatter grid (105) transmits two distinct beams of x-rays (106). The two distinct transmitted beams of x-rays (106) create alternating images on a sensor material (107) positioned on a side of the anti-scatter grid (105) opposite the x-ray source (101). A stereo radiographic image is created from the alternating images on the sensor material (107).

BRIEF DESCRIPTION OF THE DRAWINGS

These and other more detailed and specific objects and features of the present invention and more fully disclosed in the following specification, reference being had to the accompanying drawings, in which.

DETAILED DESCRIPTION OF THE PREFERRED EMBODIMENTS

Figure 1:
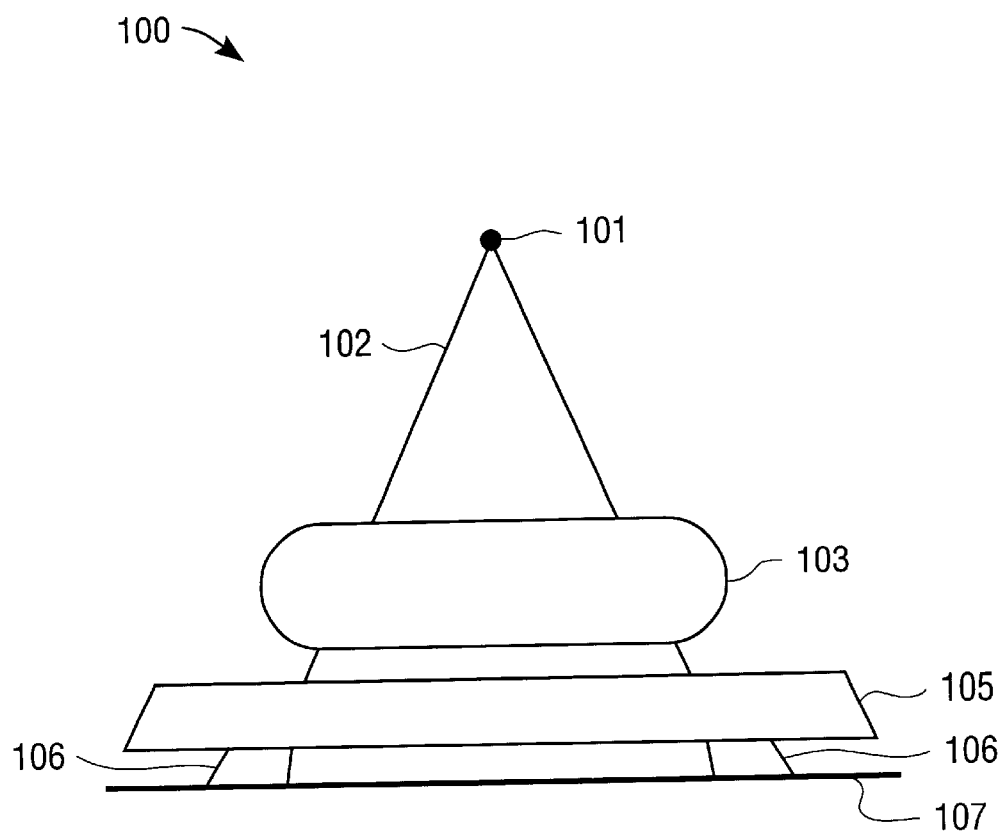
FIG. 1 is a high level schematic diagram illustrating an overview of a preferred embodiment of the present invention for using an anti-scatter grid to produce a stereo image in a radiography system.

FIG. 1 is a high level schematic diagram illustrating an overview of a preferred embodiment of the present invention for using an anti-scatter grid 105 to produce a stereo image in a radiography system. An x-ray source 101 emits a beam of x-rays 102 towards a body 103 to be radiographed. An anti-scatter grid 105 is focused such that it transmits two distinct beams of x-rays 106 to a sensor material 107. The sensor material 107 is positioned on a side of the anti-scatter grid 105 opposite the x-ray source 101. The two distinct transmitted beams of x-rays 106 create alternating images on the sensor material 107. In a preferred embodiment of the present invention, the sensor material 107 comprises a digital sensor plate. In alternative embodiments, the sensor material 107 comprises film. In all embodiments, a stereo radiographic image is created from the alternating images on the sensor material 107.

Figure 2:
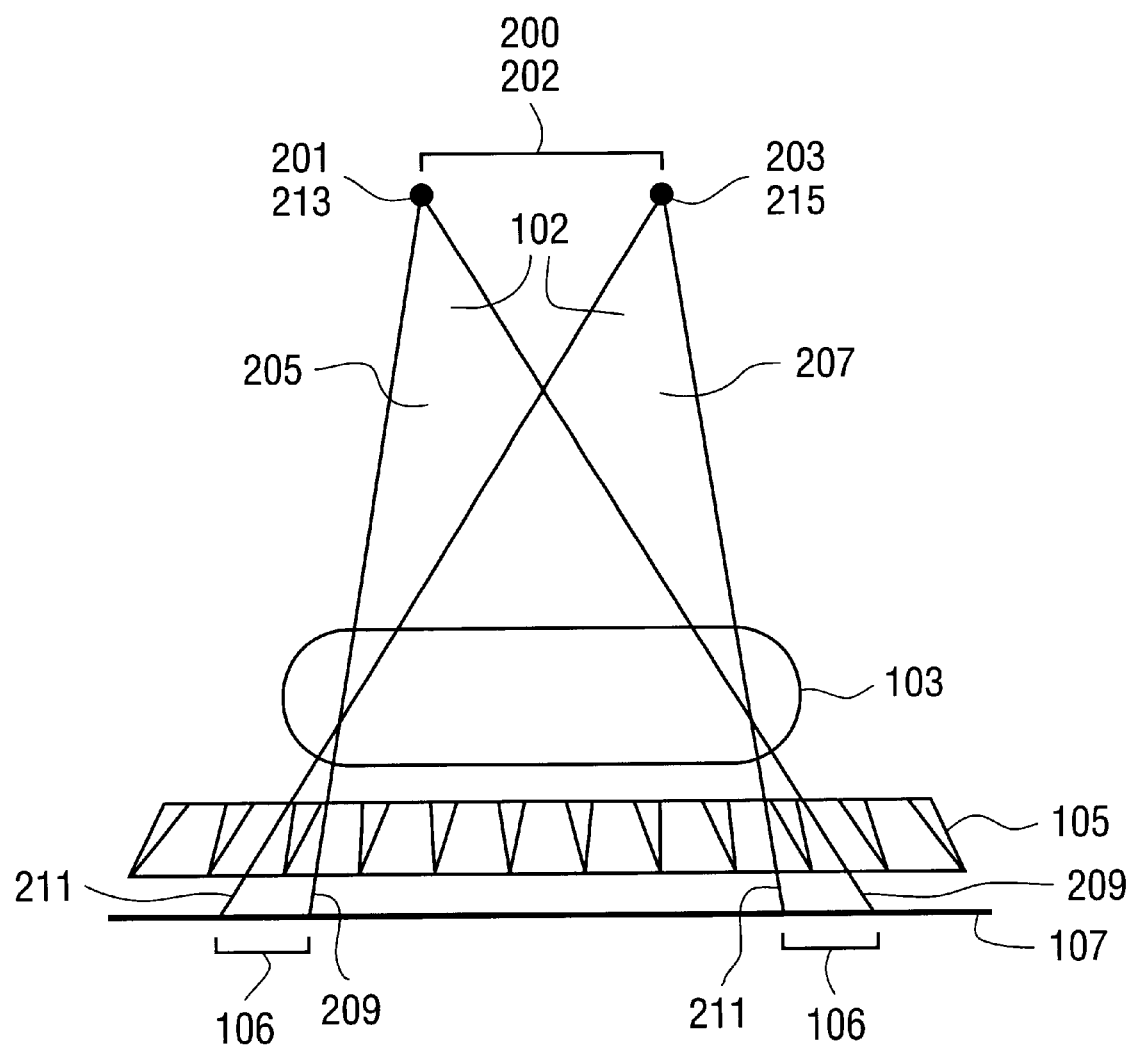
FIG. 2 is a schematic diagram illustrating a radiography system with two x-ray sources, in a preferred embodiment of the present invention.

FIG. 2 is a schematic diagram illustrating a preferred embodiment of the present invention. Two separate x-ray sources 200 are positioned on a side of the anti-scatter grid 105 opposite the sensor material 107, a first x-ray source 201 being positioned at a first focal point 213 associated with the anti-scatter grid 105, and a second x-ray source 203 being positioned at a separate, second focal point 215, also associated with the anti-scatter grid 105. The first x-ray source 201 is positioned at a focal point 213 to the left of the focal point 215 at which the second x-ray source 203 is positioned, from the perspective of the orientation depicted in FIG. 2.

In a preferred embodiment of the present invention, an imaginary line extended from the left focal point 213 associated with the anti-scatter grid 105 to the right focal point 215 associated with the anti-scatter grid 105 is parallel to the surface of the sensor material 107. In alternative embodiments, said imaginary line is not parallel to the surface of the sensor material 107. In other words, in alternative embodiments each of the two focal points 202 is described by a different coordinate on an axis perpendicular to the surface of the sensor material 107.

A focal point associated with an anti-scatter grid 105 is a point at which imaginary straight lines would intersect, the lines being extended from the points at which the progressively angled radiopaque sections of the anti-scatter grid 105 intersect with the surface of the anti-scatter grid 105. In the present invention, the internal radiopaque sections of the anti-scatter grid 105 are progressively angled such that two distinct focal points 202 are associated with the anti-scatter grid 105. The focusing of the anti-scatter grid 105 is explained in greater detail later in this section.

X-ray beams 102 are emitted from the left x-ray source 201 and from the right x-ray source 203. Preferably, the x-ray beams 102 are emitted simultaneously. In alternative embodiments, the x-ray beams 102 from the left x-ray source 201 and the from the right x-ray source 203 are emitted at distinct times as desired. In any case, the x-ray beams 102 travel through the body 103 being radiographed, to the anti-scatter grid 105. The anti-scatter grid 105 is focused so as to transmit two distinct beams of x-rays 106 to the sensor material 107, one beam 209 comprising x-rays traveling in the direction of the x-ray beam 205 from the left x-ray source 201, and the other beam 211 comprising x-rays traveling in the direction of the beam 207 from the right x-ray source 203. The sensor material 107 is positioned on a side of the anti-scatter grid 105 opposite the two x-ray sources 200. As noted above, the focusing of the anti-scatter grid 105 is explained in detail later in this section.

In a preferred embodiment of the present invention, the sensor material 107 comprises a digital sensor plate. In alternative embodiments, the sensor material 107 comprises film as desired. In either case, the two distinct x-ray beams 106 transmitted by the anti-scatter grid 105 reach the sensor material 107, and form two distinct, alternating images thereon, one image associated with the x-ray beam 205 from the left x-ray source 201, and the other image associated with the x-ray beam 207 from the right x-ray source 203.

Figure 3:
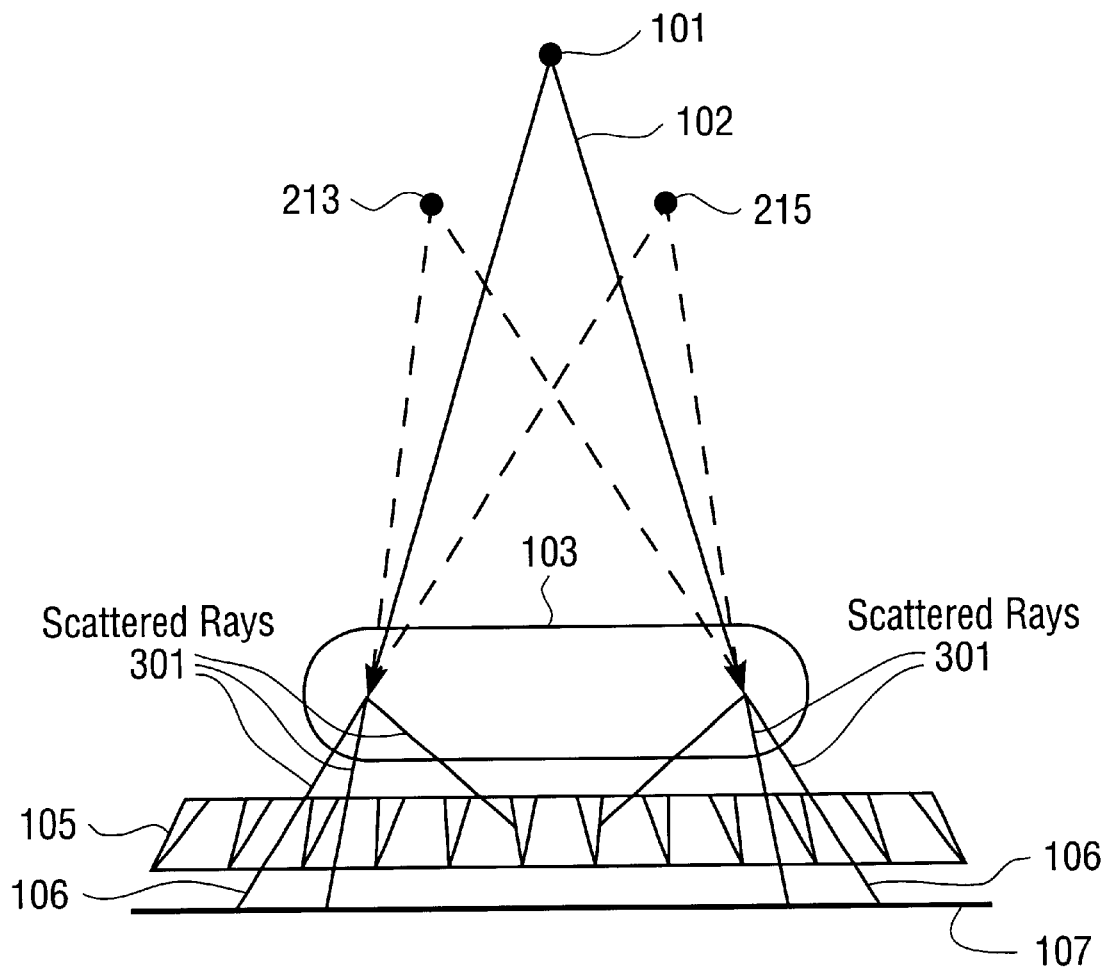
FIG. 3 is a schematic diagram illustrating a radiography system with two focal points and a single x-ray source, in an alternative embodiment of the present invention.

FIG. 3 is a schematic diagram illustrating an alternative embodiment of the present invention. When dense body sections are radiographed, a large quantity of scattered radiation 301 is produced. Because of this large quantity of scattered radiation 301, two x-ray sources 200 are not needed when a dense body section is radiographed. Instead, a single x-ray source 101 is utilized. Preferably, the single x-ray source 101 is positioned between the two separate focal points 202 for the anti-scatter grid 105. In alternative embodiments, the single x-ray source 101 is positioned at alternative locations as desired. In any case, x-rays are emitted from the source 101, and scattered in all directions by the body 103. Because these x-rays are traveling in all directions relative to the body 103, x-rays are traveling in the directions in which primary beams 102 would be traveling, were they to be emitted from x-ray sources at the left 213 and right 215 focal points associated with the anti-scatter grid 105.

The x-rays traveling in these directions are then transmitted by the focused anti-scatter grid 105 to the sensor material 107. The sensor material 107 is positioned on a side of the anti-scatter grid 105 opposite the x-ray source 101. The two distinct x-ray beams 106 transmitted by the anti-scatter grid 105 reach the sensor material 107, and form two distinct, alternating images thereon. Thus, a single x-ray source 101 mimics the origination of x-rays from two distinct sources 200.

In another alternative embodiment of the present invention, a single x-ray source 101 is first positioned at a single focal point 213 associated with the anti-scatter grid 105. The source 101 emits a single beam of x-rays 205, which is transmitted by the anti-scatter grid 105, creating a single image on the sensor material 107. The x-ray source 101 is then repositioned to a second focal point 215 associated with the anti-scatter grid 105. The source 101 again emits a single beam of x-rays 207, traveling in a direction other than that of the previously emitted beam 205. The second beam of x-rays 207 is transmitted by the anti-scatter grid 105, creating a second image on the sensor material 107, the second image alternating with the first.

Figure 4:
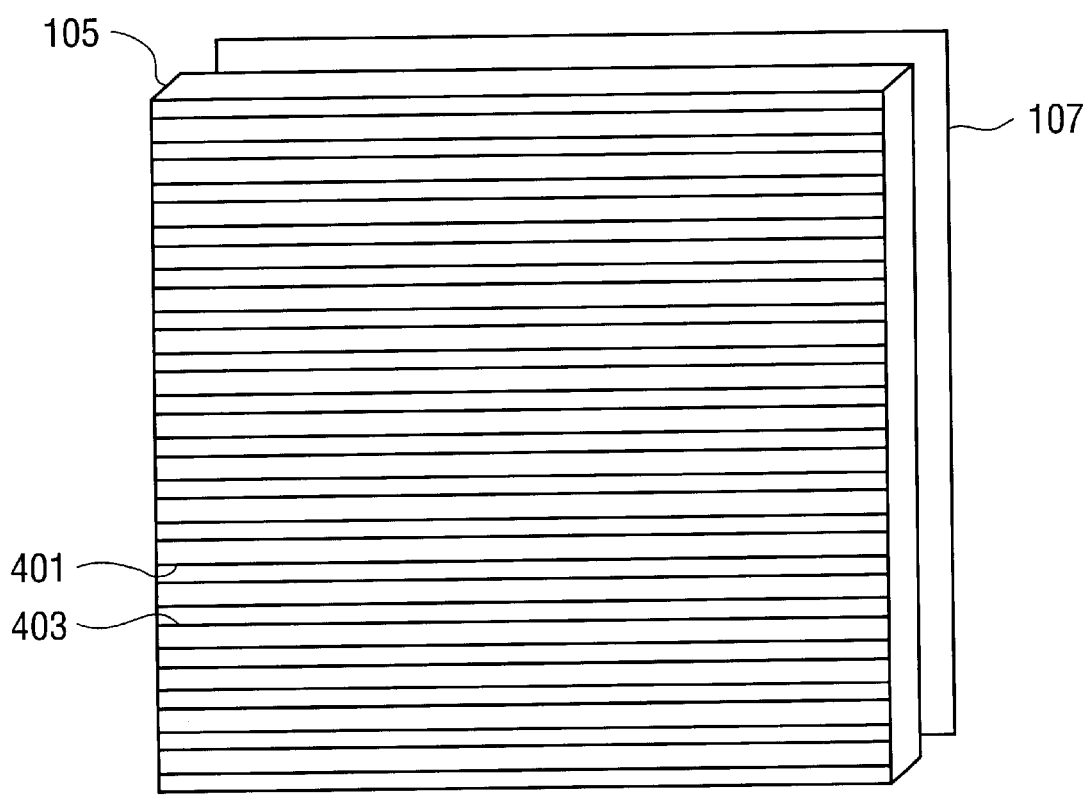
FIG. 4 is a schematic diagram illustrating a focused stereo anti-scatter grid in a preferred embodiment of the present invention.

FIG. 4 illustrates a focused anti-scatter grid 105 in a preferred embodiment of the present invention. The anti-scatter grid 105 contains radiopaque strips focused for the left focal point 213 associated with the anti-scatter grid 105 and for the right focal point 215 associated with the anti-scatter grid 105. Radiopaque strips focused 401 for the left focal point 213 associated with the anti-scatter grid 105 alternate with radiopaque strips focused 403 for the right focal point 215 associated with the anti-scatter grid 105. The strips focused 401 for the left focal point 213 transmit radiation traveling in the direction of the beam 205 from the left x-ray source 201. The strips focused 403 for the right focal point 215 transmit radiation traveling in the direction of the beam 207 from the right x-ray source 203. Thus, the strips focused 401 so as to transmit radiation traveling in the direction of the beam 205 from the left x-ray source 201 alternate with the strips focused 403 so as to transmit radiation traveling in the direction of the beam 207 from the right x-ray source 203. Therefore, two alternating horizontal images are created on the sensor material 107, one image being associated with the left focal point 213 and the other image being associated with the right focal point 215.

In a preferred embodiment of the present invention, the sensor material 107 comprises a digital sensor plate. A digital file is created from the radiographic images on the digital sensor plate. The two alternating horizontal images are separated. There will be some space between the images. Roughly fifty percent of the space between the images is assigned to the image associated with the left focal point 213, and roughly fifty percent of the space is assigned to the image associated with the right focal point 215. Two distinct stereo images result. The stereo image pair can be viewed on a standard stereo display or any other standard stereo viewing equipment.

In a preferred embodiment of the present invention, the creation of the digital file, the separation of the alternating horizontal images, and the assigning of the space between the horizontal images are all performed by computer software. In alternative embodiments, these steps are performed by firmware, hardware, or any combination of software, firmware, and hardware.

In an alternative embodiment of the present invention, the sensor material 107 comprises film. In such an embodiment, the film is scanned, and a digital file is created from the scanned image. The digital file is then processed as described above.

Figure 5:
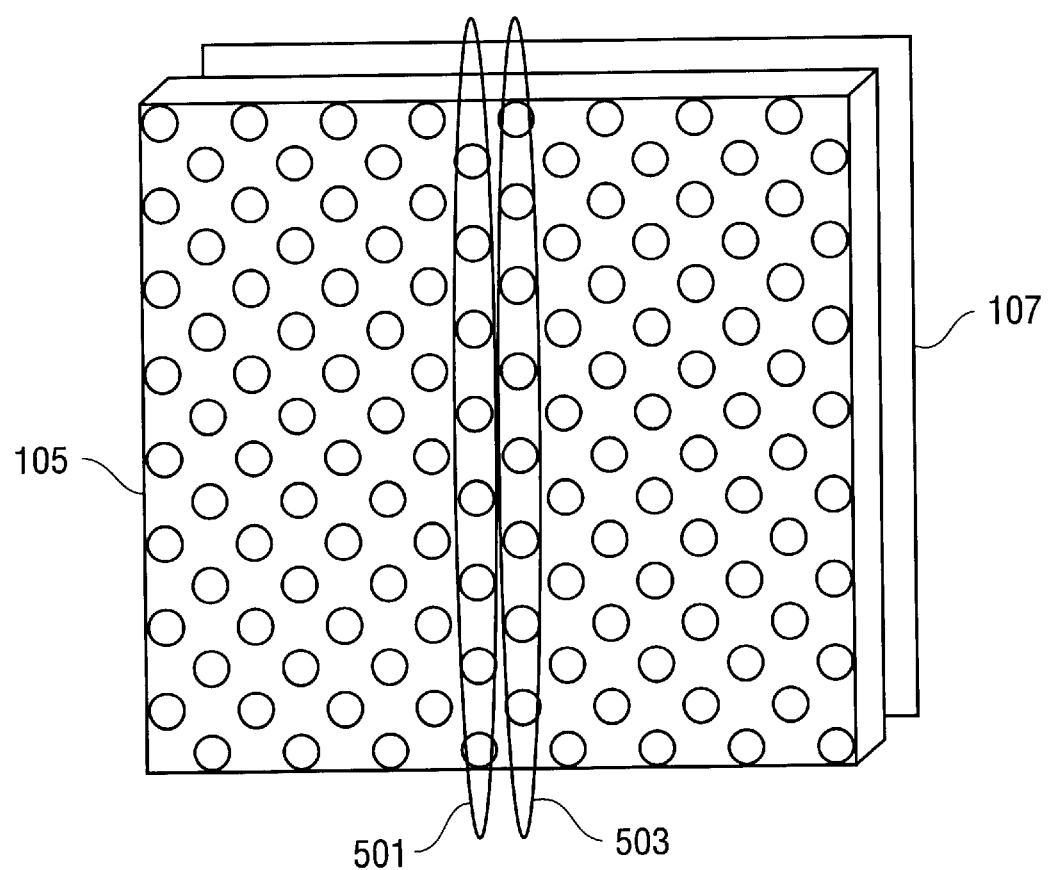
FIG. 5 is a schematic diagram illustrating a focused stereo anti-scatter grid in an alternative embodiment of the present invention.

FIG. 5 illustrates a focused anti-scatter grid 105 in an alternative embodiment of the present invention. The anti-scatter grid 105 contains radiopaque strips focused for the left focal point 213 associated with the anti-scatter grid 105 and for the right focal point 215 associated with the anti-scatter grid 105. Each strip comprises discontinuous sections of radiopaque material. The strips are focused alternatively for the left focal point 213 of the anti-scatter grid 105 and the right focal point 215 of the anti-scatter grid 105. The alternating strips are positioned such that the discontinuous sections of radiopaque material of a strip focused 501 for the left focal point 213 are adjacent to areas between the discontinuous sections of radiopaque material of a strip focused 503 for the right focal point 215. Therefore, the anti-scatter grid 105 transmits x-rays so as to create alternating horizontal and vertical images for the left 213 and right 215 focal points on the sensor material 107. Both vertical and horizontal resolution is lost, but the result is a stereo radiographic image.

The preferable sensor material 107 for use with the anti-scatter grid 105 depicted in FIG. 5 is film. The stereo image from the film is viewed through the use of a set of vertical plastic lenses, placed on top of the image. The image comprises alternating right eye columns and left eye columns. The lenses allow each eye to see every other column of the image. This known technique for viewing a stereo image is called a lenticular viewer. Lenticular viewers are used to view stereo postcards, posters, and the like.

Alternatively, the sensor material 107 to be used with the anti-scatter grid 105 depicted in FIG. 5 comprises a digital sensor plate. In such an embodiment, a digital file is created from the image on the sensor plate. A stereo image is then created from the information in the digital file. The resulting stereo image is viewed with a lenticular viewer as described above.

In alternative embodiments, other anti-scatter grids 105 are utilized in order to create a stereo radiographic image.

Preferably, the stereo anti-scatter grid 105 is removable. The radiography system accommodates the use of a non-stereo anti-scatter grid 105 in the space vacated by the removed stereo grid 105. Thus, the radiography system can be used to create non stereo images as well as stereo images.

The geometry of the stereo radiography system is known, so it is possible to determine an exact location of an object 606 within a radiographed body 103 from the location of the object 606 in the radiograph.

Figure 6:
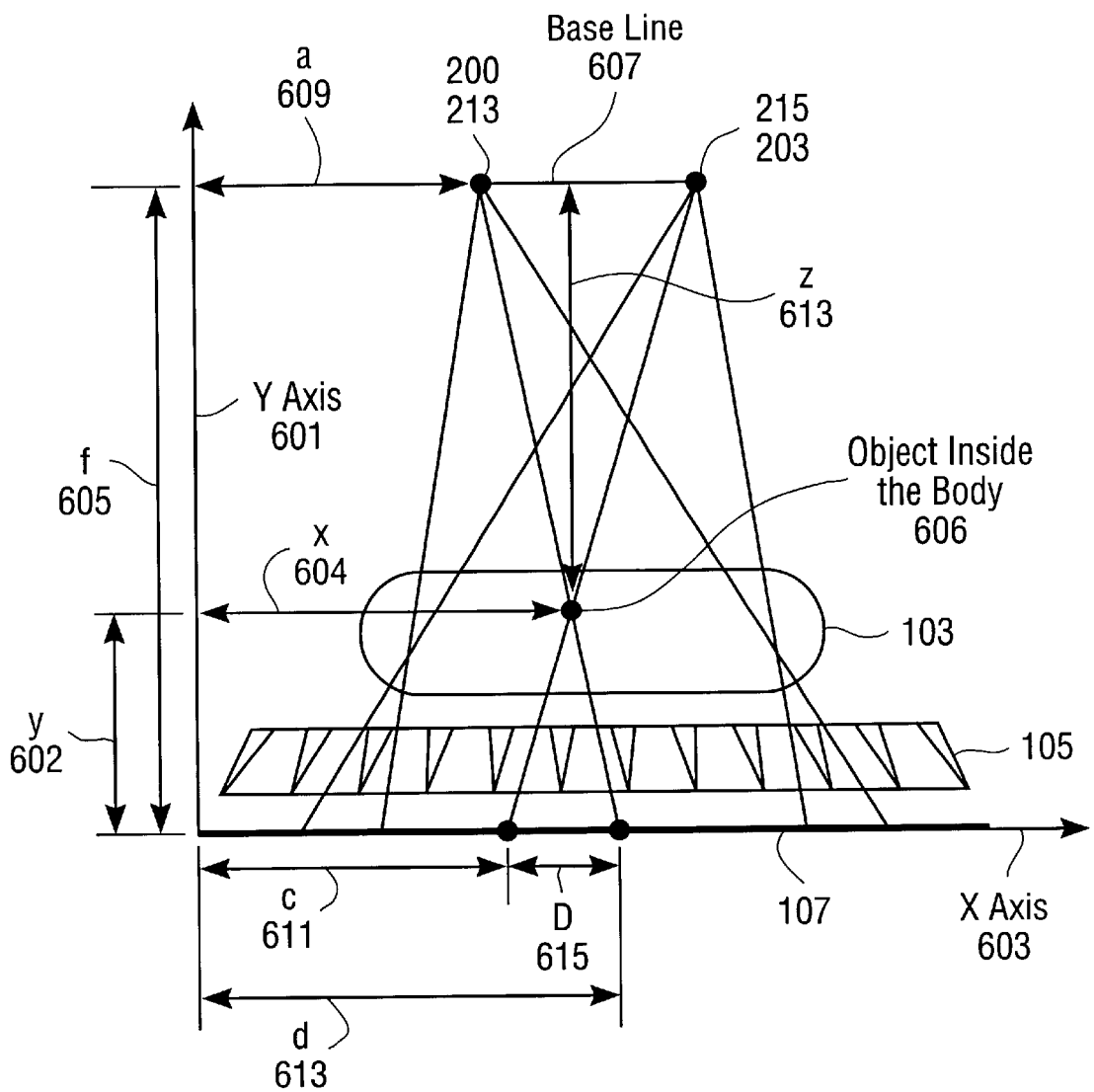
FIG. 6 is a schematic diagram illustrating system geometry of a radiography system in a preferred embodiment of the present invention.

FIG. 6 illustrates a coordinate system XY in a preferred embodiment of the present invention. The Y-axis 601 is perpendicular to the surface of the sensor material 107 and the X-axis 603 is parallel thereto. In this system, y 602 and x 604 are the coordinates of an object 606 inside a radiographed body 103. In a preferred embodiment, the geometry of the system gives us the following necessary relationships between parameters:

$$\frac{a+b-c}{f} = \frac{x-c}{y}, \frac{d-a}{f} = \frac{d-x}{y},$$

where f (the focal length) is the distance 605 between the two focal points 202 and the surface of the sensor material 107 (in a preferred embodiment both of the focal points 202 are located the same distance from the surface of the sensor material 107), b (the base line) is the distance 607 between the two focal points 202, a 609 is the X coordinate of the left focal point 213, and c and d are the X coordinates of the object 606 in the right 611 and left 613 images on the sensor material respectively. The coordinates y 602 and x 604 are calculated as follows:

$$x = \frac{da + db - dc}{b + d - c}, y = f\frac{d-c}{b+d-c}$$

In a preferred embodiment of the present invention, the focal length 605, the base line 607, the left focal point 213 X coordinate 609, and the X coordinates of the object 606 in the right 611 and left 613 images on the sensor material 107 are all determined automatically. Preferably, such automatic determination is conducted by a combination of hardware and software. In alternative embodiments, such determination is conducted by software, hardware, firmware, or any combination of the three as desired. In an alternative embodiment of the present invention, some or all of said determinations are conducted manually.

Preferably, the calculation to determine the coordinates of the object 606 is performed automatically. In a preferred embodiment of the present invention, such automatic calculation is performed by computer software. In alternative embodiments, such automatic calculation is performed by hardware or firmware, or any combination of software, hardware, and firmware, as desired. In an alternative embodiment of the present invention, the calculation is performed manually.

Preferably, once the location of the object 606 is determined, the location is displayed on a video screen or the like to a user of the radiography system. In alternative embodiments, the location of the object 606 is communicated by the system in other ways, such as the generation of a printed report.

In alternative embodiments of the present invention with differences in focal point position and the like, system geometry will vary slightly. In said embodiments, similar formulas are derived from the system geometry to determine the coordinates of the object 606 in the body being radiographed 103.

The system geometry is also used to determine a distance 613 from a chosen point to an object 606 in the radiographed body 103. The basic concept of stereo is matching pairs. Thus, the system uses the distance between images of an object 606 in the alternating left and right images on the sensor material (the disparity) 615 to calculate the distance 613 from a chosen point to the object 606 in the radiographed body 103. For example, in a preferred embodiment of the present invention, the base line 607 is parallel to the surface of the sensor material 107. Because the two focal points 202 are described by an identical coordinate on the y axis 601, the distance 613 from the object 606 to the base line 607 is inversely proportional to the disparity 615. The formula is $z=fb/D$, where z is the distance 613 from the object 606 to the base line 607, f is the focal length 605, which in the preferred embodiment of this example is the same for both focal points 202, b is the distance between focal points (the base line) 607, and D is the disparity 615. The system geometry is utilized to determine similar formulas to calculate the distance from other chosen points to the object 606 in the radiographed body 103.

In a preferred embodiment of the present invention, the focal length 605, the base line 607, and the disparity 615 are all determined automatically. Preferably, such automatic determination is conducted by a combination of hardware and software. In alternative embodiments, such determination is conducted by software, hardware, firmware, or any combination of the three as desired. In an alternative embodiment of the present invention, some or all of said determinations are conducted manually.

Preferably, the calculation to determine the distance 613 from a chosen point to an object 606 in the radiographed body 103 is performed automatically. In a preferred embodiment of the present invention, such automatic calculation is performed by computer software. In alternative embodiments, such automatic calculation is performed by hardware or firmware, or any combination of software, hardware, and firmware, as desired. In an alternative embodiment of the present invention, the calculation is performed manually.

Preferably, once the calculation has been performed, the result of the calculation is displayed on a video screen or the like to a user of the radiography system. In alternative embodiments, the result of the calculation is communicated by the system in other ways, such as the generation of a printed report.

In alternative embodiments of the present invention with differences in focal point position and the like, system geometry will vary slightly. In said embodiments, similar formulas are derived from the system geometry to determine the distance between a chosen point and the object 606 in the body being radiographed 103.

There is a difficulty associated with determining that two points in the alternating images on the sensor material correspond to the same object 606. Such a determination is necessary in order to determine the X coordinates of the object 606 in the right 611 and left 613 images on the sensor material, as well as to determine the disparity 615. The difficulty is a result of the nature of radiographs. Unlike a photograph, which is a reflection of an object, a radiograph is instead a projection of many objects. When an x-ray passes through a body 103, it projects an image of every point through which it passes. Thus, an image on a radiograph can represent multiple points in a body 103.

The difficulty is solved in the present invention by employing known, standard techniques to match objects from stereo pairs. One such technique is template matching, in which an algorithm matches objects in stereo images by correlating gray levels. Another technique is feature matching, in which an algorithm extracts salient primitives from the stereo images, such as edge segments and contours. The algorithm proceeds to match the primitives in the two images.

The extraction of primitives is called segmentation. The simplest method is based on identifying groups of pixels with similar features such as brightness, color, and the like. Similar groups of adjacent pixels are thus isolated.

The above description is included to illustrate the operation of the preferred embodiments and is not meant to limit the scope of the invention. The scope of the invention is to be limited only by the following claims. From the above discussion, many variations will be apparent to one skilled in the art that would yet be encompassed by the spirit and scope of the present invention.

What is claimed is:

1. In a radiography system including an anti-scatter grid, a method for producing a stereo radiograph, the method comprising:

emitting a beam of x-rays towards a body to be radiographed;

focusing the anti-scatter grid such that the grid transmits two distinct beams of x-rays so as to create two alternating images on a single sensor material, the sensor material being positioned on a side of the anti-scatter grid opposite the body to be radiographed; and creating a stereo radiographic image from the two alternating images on the sensor material.

2. The method of claim 1 further comprising:

positioning two separate x-ray sources, each source being positioned at a separate focal point associated with the anti-scatter grid;

emitting x-rays from the two sources; and creating, from x-rays emitted by the two sources and transmitted by the anti-scatter grid, alternating images on a single sensor material.

3. The method of claim 1 further comprising:

positioning a single x-ray source on a side of the anti-scatter grid opposite the sensor material;

emitting x-rays from the source;

transmitting the x-rays by the anti-scatter grid such that the x-rays travel to the sensor material in two directionally distinct beams, mimicking the origination of x-rays from two separate sources positioned at two separate focal points of the grid; and creating, from the x-rays emitted by the single source and transmitted by the anti-scatter grid, alternating images on a single sensor material.

4. The method of claim 1 further comprising:

positioning a single x-ray source at a focal point associated with the anti-scatter grid;

emitting x-rays from the source;

creating, from the x-rays emitted by the single source and transmitted by the anti-scatter grid, a single image on a single sensor material;

repositioning the single x-ray source at a second focal point associated with the anti-scatter grid;

emitting x-rays from the source; and creating, from the x-rays emitted by the single source and transmitted by the anti-scatter grid, a second image on the single sensor material, the second image alternating with the first image.

5. The method of claim 1 further comprising:

including in the anti-scatter grid radiopaque strips;

focusing the radiopaque strips alternatively for a left focal point of the anti-scatter grid and a right focal point of the anti-scatter grid; and transmitting x-rays by the focused anti-scatter grid so as to create alternating horizontal images for the left and right focal points on the sensor material.

6. The method of claim 5, wherein the sensor material is a digital sensor plate, and the method further comprises:

creating a digital file from the radiographic image on the sensor material, the digital file comprising the alternating horizontal images for the left and right focal points of the anti-scatter grid;

separating the alternating horizontal images;

assigning roughly fifty percent of areas between the horizontal images to the image for the left focal point;

assigning roughly fifty percent of areas between the horizontal images to the image for the right focal point; and creating two digital stereo images.

7. The method of claim 5, wherein the sensor material is film, and the method further comprises:

scanning the film;

creating a digital file from the scanned image, the digital file comprising the alternating horizontal images for the left and right focal points of the anti-scatter grid;

separating the alternating horizontal images;

assigning roughly fifty percent of areas between the horizontal images to the image for the left focal point;

assigning roughly fifty percent of areas between the horizontal images to the image for the right focal point; and creating two digital stereo images.

8. The method of claim 1 further comprising:

including in the anti-scatter grid radiopaque strips, each strip comprising discontinuous sections of radiopaque material;

focusing the radiopaque strips alternatively for a left focal point of the anti-scatter grid and a right focal point of the anti-scatter grid;

positioning the alternating strips such that the discontinuous sections of radiopaque material of a strip focused for the left focal point are adjacent to areas between the discontinuous sections of radiopaque material of a strip focused for the right focal point; and transmitting x-rays by the anti-scatter grid so as to create alternating horizontal and vertical images for the left and right focal points on the sensor material.

9. In a radiography system including an anti-scatter grid with two associated focal points, and including a sensor material with a surface, a method for determining a location of an object in a radiographed body, the method comprising:

determining a distance between a left focal point associated with the anti-scatter grid and a right focal point associated with the anti-scatter grid;

determining a distance between a line connecting the two focal points associated with the anti-scatter grid and the surface of the sensor material;

determining a location of the left focal point on a horizontal axis parallel to the surface of the sensor material;

determining a location of the object in a radiographic image associated with the left focal point;

determining a location of the object in a radiographic image associated with the right focal point;

applying a geometry of the radiography system to calculate the location of the object within the body; and communicating the calculation result to a user of the radiography system.

10. In a radiography system including an anti-scatter grid with two associated focal points, and including sensor material with a surface, a method for determining a distance between a chosen point and an object in a radiographed body, the method comprising:

determining a distance between a representation of the object in an image associated with the left focal point and a representation of the object in an image associated with the right focal point;

applying a geometry of the radiography system to calculate the distance between the chosen point and the object; and communicating the calculation result to a user of the radiography system.

11. The method of claim 10, further comprising:

determining a distance between a left focal point associated with the anti-scatter grid and a right focal point associated with the anti-scatter grid;

determining a distance between a line connecting the two focal points associated with the anti-scatter grid and the surface of the sensor material; and applying a geometry of the radiography system to calculate the distance between a chosen point on the line connecting the two focal points associated with the anti-scatter grid and the object.

12. A radiography system for producing a stereo radiograph, the system comprising:

an x-ray source, for emitting a beam of x-rays towards a body to be radiographed;

an anti-scatter grid, focused such that the grid transmits two distinct beams of x-rays so as to create two alternating images on a single sensor material, the anti-scatter grid being positioned on a side of the body to be radiographed opposite the x-ray source; and a sensor material, for creating a stereo radiographic image in response to the two alternating images, the sensor material being positioned on a side of the anti-scatter grid opposite the x-ray source.

13. The radiography system of claim 12 further comprising:

two separate x-ray sources for emitting beams of x-rays towards a body to be radiographed, each source being positioned at a separate focal point associated with the anti-scatter grid; and a creation module, for creating, from the x-rays emitted by the two sources and transmitted by the anti-scatter grid, alternating images on the sensor material, the creation module being coupled to the sensor material.

14. The radiography system of claim 12 further comprising:

a single x-ray source for emitting beams of x-rays towards a body to be radiographed, the x-ray source being positioned on a side of the body to be radiographed opposite the sensor material;

an anti-scatter grid for transmitting x-rays to the sensor material in two directionally distinct beams, mimicking the origination of x-rays from two separate sources positioned at two separate focal points of the grid, the anti-scatter grid being positioned between the sensor material and the body to be radiographed; and a creation module, for creating, from the x-rays emitted by the x-ray source and transmitted by the anti-scatter grid, alternating images on the sensor material, the creation module being coupled to the sensor material.

15. The radiography system of claim 12 further comprising:

a single x-ray source, the source being movable, for positioning alternately at two separate focal points associated with the anti-scatter grid, and for emitting beams of x-rays towards a body to be radiographed; and a creation module, for creating, from the x-rays emitted by the x-ray source and transmitted by the anti-scatter grid, a single image on the sensor material, the creation module being coupled to the sensor material.

16. The radiography system of claim 12 further comprising:

an anti-scatter grid including radiopaque strips, the strips being alternatively focused for a left focal point of the anti-scatter grid and a right focal point of the anti-scatter grid, for transmitting x-rays so as to create alternating horizontal images for the left and right focal points on the sensor material.

17. The radiography system of claim 16 wherein the sensor material comprises a digital sensor plate coupled to the anti-scatter grid, and the system further comprises:

a file creation module for creating a digital file comprising the alternating horizontal images for the left and right focal points of the anti-scatter grid, the file creation module being coupled to the sensor material;

a separation module for separating the alternating horizontal images, the separation module being coupled to the file creation module;

an assignment module for assigning roughly fifty percent of areas between the horizontal images to the image for the left focal point, and for assigning roughly fifty percent of areas between the horizontal images to the image for the right focal point, the assignment module being coupled to the separation module; and an image creation module for creating two digital stereo images, the image creation module being coupled to the assignment module.

18. The radiography system of claim 16, wherein the sensor material comprises film, and the system further comprises:

a scan module for scanning the film;

a file creation module for creating a digital file from the scanned image, the digital file comprising the alternating horizontal images for the left and right focal points of the anti-scatter grid, the file creation module being coupled to the scan module and to the sensor material;

a separation module for separating the alternating horizontal images, the separation module being coupled to the file creation module;

an assignment module for assigning roughly fifty percent of areas between the horizontal images to the image for the left focal point, and for assigning roughly fifty percent of areas between the horizontal images to the image for the right focal point, the assignment module being coupled to the separation module; and an image creation module for creating two digital stereo images, the image creation module being coupled to the assignment module.

19. The radiography system of claim 12 further comprising:

an anti-scatter grid including radiopaque strips, the strips being alternatively focused for a left focal point of the anti-scatter grid and a right focal point of the anti-scatter grid, each strip comprising discontinuous sections, for transmitting x-rays so as to create alternating horizontal and vertical images for the left and right focal points on the sensor material, the alternating strips being positioned such that the discontinuous sections of radiopaque material of a strip focused for the left focal point are adjacent to areas between the discontinuous sections of radiopaque material of a strip focused for the right focal point.

20. The radiography system of claim 12, wherein:

the anti-scatter grid is removable; and the radiography system accommodates the use of a non-stereo anti-scatter grid in a space vacated by the removed anti-scatter grid.

21. A radiography system for determining a location of an object in a radiographed body, the system comprising:

an anti-scatter grid focused such that a left focal point is associated with the anti-scatter grid, and a right focal point is associated with the anti-scatter grid;

a sensor material with a surface, the sensor material being positioned on a side of the anti-scatter grid opposite the focal points;

a distance determination module, for determining a distance between the two focal points associated with the anti-scatter grid, and for determining a distance between a line connecting the two focal points associated with the anti-scatter grid and the surface of the sensor material;

a location determination module, for determining a location of the left focal point on a horizontal axis parallel to the surface of the sensor material, for determining a location of the object in a radiographic image associated with the left focal point, and for determining a location of the object in a radiographic image associated with the right focal point, the location determination module being coupled to the distance determination module;

a geometry application module, for applying a geometry of the radiography system to the determined distances and locations, the geometry application module being coupled to the location determination module;

a calculation module, for calculating the location of the object within the body based upon said application of the system geometry, the calculation module being coupled to the geometry application module; and a communication module for communicating the calculation result to a user of the radiography system, the communication module being coupled to the calculation module.

22. A radiography system for determining a distance between a chosen point and an object in a radiographed body, the system comprising:
- an anti-scatter grid focused such that a left focal point is associated with the anti-scatter grid, and a right focal point is associated with the anti-scatter grid;
- a sensor material with a surface, the sensor material being positioned on a side of the anti-scatter grid opposite the focal points;
- a disparity determination module, for determining a distance between a representation of the object in an image associated with the left focal point and a representation of the object in an image associated with the right focal point;
- a geometry application module, for applying a geometry of the radiography system, the geometry application module being coupled to the disparity determination module;
- a calculation module, for calculating the distance between the chosen point and the object within the body based upon said application of the system geometry, the calculation module being coupled to the geometry application module; and
- a communication module for communicating the calculation result to a user of the radiography system, the communication module being coupled to the calculation module.

23. The radiography system of claim 22 further comprising:
- a distance determination module for determining a distance between the two focal points associated with the anti-scatter grid, and for determining a distance between a line connecting the two focal points associated with the anti-scatter grid and the surface of the sensor material; and
- a geometry application module, for applying a geometry of the radiography system to determined distances and disparity, the geometry application module being coupled to the disparity determination module;
- a calculation module, for calculating the distance between a chosen point on the line between the two focal points associated with the anti-scatter grid and the object within the body based upon said application of the system geometry, the calculation module being coupled to the geometry application module.

24. A computer readable medium containing a computer program product for producing a stereo radiograph in a radiography system including an anti-scatter grid and sensor material comprised of a digital sensor plate, the computer program product comprising:
- program code for creating a digital file from the radiographic image on the sensor material, the digital file comprising alternating horizontal images for a left focal point of the anti-scatter grid and for a right focal point of the anti-scatter grid;
- program code for separating the alternating horizontal images;
- program code for assigning roughly fifty percent of areas between the horizontal images to the image for the left focal point;
- program code for assigning roughly fifty percent of areas between the horizontal images to the image for the right focal point; and
- program code for creating two digital stereo images on the sensor material.

25. A computer readable medium containing a computer program product for producing a stereo radiograph in a radiography system including an anti-scatter grid and sensor material comprised of film, the computer program product comprising:
- program code for scanning the film;
- program code for creating a digital file from the scanned image, the digital file comprising alternating horizontal images for a left focal point of the anti-scatter grid and for a right focal point of the anti-scatter grid;
- program code for separating the alternating horizontal images;
- program code for assigning roughly fifty percent of areas between the horizontal images to the image for the left focal point;
- program code for assigning roughly fifty percent of areas between the horizontal images to the image for the right focal point; and
- program code for creating two digital stereo images on the sensor material.

26. A computer readable medium containing a computer program product for determining a location of an object in a radiographed body in a radiography system including an anti-scatter grid with two associated focal points, and including a sensor material with a surface, the computer program product comprising:
- program code for determining a distance between a left focal point associated with the anti-scatter grid and a right focal point associated with the anti-scatter grid;
- program code for determining a distance between a line connecting the two focal points associated with the anti-scatter grid and the surface of the sensor material;
- program code for determining a location of the left focal point on a horizontal axis parallel to the surface of the sensor material;
- program code for determining a location of the object in a radiographic image associated with the left focal point;
- program code for determining a location of the object in a radiographic image associated with the right focal point;
- program code for applying a geometry of the radiography system to calculate the location of the object within the body; and
- program code for communicating the calculation result to a user of the radiography system.

27. A computer readable medium containing a computer program product for determining a distance between a chosen point and an object in a radiographed body in a radiography system including an anti-scatter grid with two associated focal points, and including sensor material with a surface, the computer program product comprising:
- program code for determining a distance between a representation of the object in an image associated with the left focal point and a representation of the object in an image associated with the right focal point;

program code for applying a geometry of the radiography system to calculate the distance between the chosen point and the object; and program code for communicating the calculation result to a user of the radiography system.

28. The computer readable medium of claim 27 further comprising:

program code for determining a distance between a left focal point associated with the anti-scatter grid and a right focal point associated with the anti-scatter grid;

program code for determining a distance between a line connecting the two focal points associated with the anti-scatter grid and the surface of the sensor material;

program code for applying a geometry of the radiography system to calculate the distance between a chosen point on the line connecting the two focal points associated with the anti-scatter grid and the object; and program code for communicating the calculation result to a user of the radiography system.

* * * * *